United States Patent [19]

Li et al.

[11] Patent Number: 4,634,035
[45] Date of Patent: Jan. 6, 1987

[54] SKIN STAPLER

[75] Inventors: Lehmann K. Li; Michael Marra, both of Fairfield, Conn.

[73] Assignee: American Cyanamid Company, Stamford, Conn.

[21] Appl. No.: 588,275

[22] Filed: Mar. 12, 1984

[51] Int. Cl.$^4$ .............................................. A61B 17/00
[52] U.S. Cl. ................................ 227/19; 128/334 R; 227/83; 227/116; 227/DIG. 1
[58] Field of Search ....... 128/334 R; 227/19, DIG. 1, 227/83, 120, 116

[56] References Cited

U.S. PATENT DOCUMENTS

| | | | |
|---|---|---|---|
| 1,945,377 | 1/1934 | Posnack | 227/DIG. 1 |
| 2,635,234 | 4/1953 | Reed | 227/89 |
| 4,043,504 | 8/1977 | Hueil et al. | 227/DIG. 1 |
| 4,185,762 | 1/1980 | Froehlich | 227/DIG. 1 |
| 4,202,480 | 5/1980 | Annett | 227/8 |
| 4,364,507 | 12/1982 | Savino | 227/DIG. 1 |
| 4,478,362 | 10/1984 | Foslien | 227/19 |
| 4,527,725 | 7/1985 | Foslien | 227/19 |

FOREIGN PATENT DOCUMENTS

| | | | |
|---|---|---|---|
| 0069557 | 1/1983 | European Pat. Off. | 227/DIG. 1 |
| 8401706 | 5/1984 | World Int. Prop. O. | 227/DIG. 1 |
| 189982 | 1/1967 | U.S.S.R. | 227/DIG. 1 |

Primary Examiner—Paul A. Bell
Attorney, Agent, or Firm—Charles F. Costello, Jr.

[57] ABSTRACT

The prior art discloses a surgical stapler having means for forming a staple, and means for activating the forming means. The forming means have an anvil surface terminating in a movable flange and a track movably containing a forming blade. The improved stapler of this invention comprises the activating means cooperatively attached to the forming means, and the anvil surface having a boss and the forming blade having an opening. The anvil surface boss has an arcuate motion dependent on the linear motion of the forming blade opening. Alternatively, the improved stapler also comprises a formed staple stripping surface adjacent at least two opposing sides of the anvil flange.

12 Claims, 7 Drawing Figures

SKIN STAPLER

BACKGROUND AND SUMMARY OF THE INVENTION

This invention relates to an improved surgical skin/fascia stapling instrument. The instrument contains a plurality of staples, and allows a single staple to be formed and removed from the instrument.

An improved surgical stapler has been invented. The stapler comprises means for forming a staple and means for activating the forming means.

The forming means have an anvil surface terminating in a movable flange and a track movably containing a forming blade. The activating means is cooperatively attached to the forming means.

The improvement comprises the anvil surface having a boss and the forming blade having an opening. The anvil surface boss has an arcuate motion which is dependent on the linear motion of the forming blade opening. The boss moves into the opening as the forming blade approaches the flange, and the boss moves out of the opening as the forming blade retracts from the flange. The anvil flange is in substantial alignment with the forming blade when the boss is in the opening so that a staple can be formed on the flange by the forming blade, and the anvil flange is taken out of alignment with the forming blade as the boss moves out of the opening.

In one embodiment, the anvil surface and flange is biased relative to the forming blade. In another embodiment, the anvil surface and flange is cantilevered.

In yet another embodiment, the forming means has a first track movably containing a plurality of staples and the forming blade is movably contained on a second track. In still another embodiment, the boss moves into the opening essentially after zero travel of the forming blade toward the anvil flange such that the anvil flange is in substantial alignment with the forming blade before or as the distal portion of the forming blade contacts the proximal staple from the plurality of staples.

Another improved surgical stapler has been invented. The stapler comprises a housing, means for forming a staple, and means for activating the forming means. The forming means has an anvil surface terminating in a movable flange and a track movably containing a forming blade. The activating means is cooperatively attached to the forming means. The improvement comprises the anvil surface having a boss, the forming blade having an opening, and, relative to the anvil flange, a formed staple stripping surface adjacent at least two opposing sides of the anvil flange. The anvil surface boss has an arcuate motion which is dependent on the linear motion of the forming blade spring. The boss moves into the opening as the forming blade approaches the flange, and the boss moves out of the opening as the forming blade retracts from the flange. The anvil flange is in substantial alignment with the forming blade when the boss is in the opening so that a staple can be formed on the flange by the forming blade, and the anvil flange is taken out of alignment with the forming blade as the boss moves out of the opening so that the formed staple on the flange can be stripped off the flange by the stationary stripping surface.

In one embodiment, the housing has a handle. In another embodiment, the housing has a magazine. In yet another embodiment, the stationary stripping surface is contained on the housing, on the handle, or on the magazine.

Other embodiments to the improved stapler are wherein the anvil surface and flange is biased relative to the forming blade; wherein the anvil surface and flange is cantilevered; wherein the forming means has a first track movably containing a plurality of staples and the forming blade is movably contained on a second track; and wherein the boss moves into the opening essentially after zero travel of the forming blade toward said anvil flange such that the anvil flange is in substantial alignment with the forming blade before or as the distal portion of the forming blade contacts the proximal staple from the plurality of staples.

DESCRIPTION OF THE PREFERRED EMBODIMENT

Figure 1:
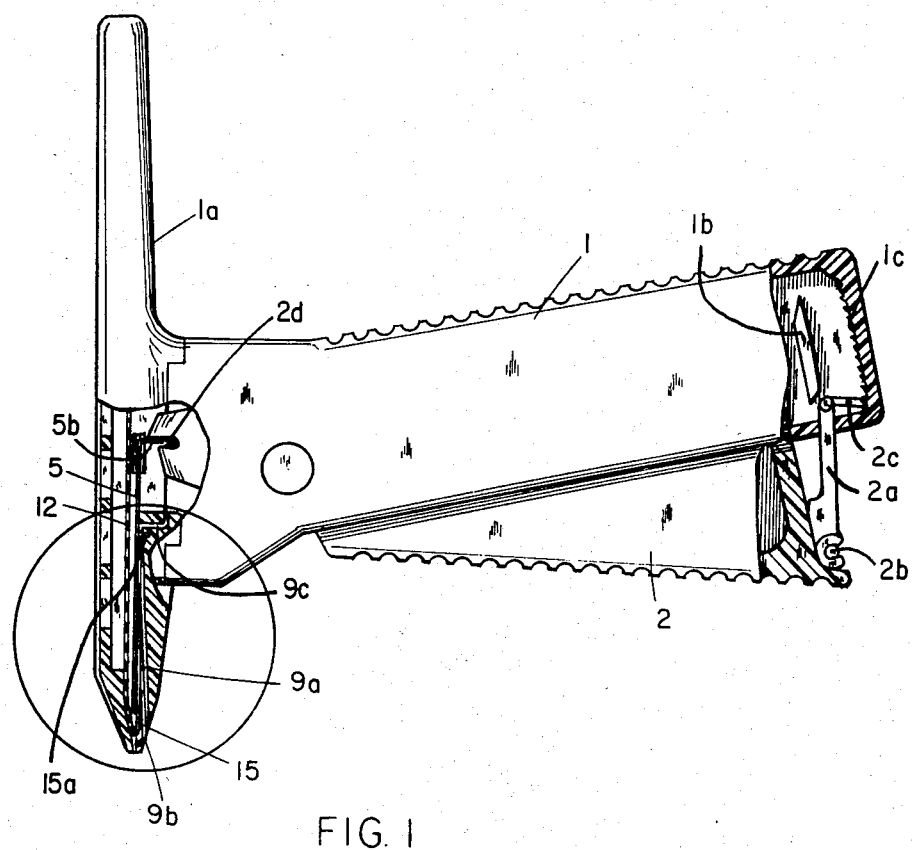
FIG. 1 is a partially cutaway side view showing the improvements, and a means to control the movement of the trigger into the handle.
Figure 2:
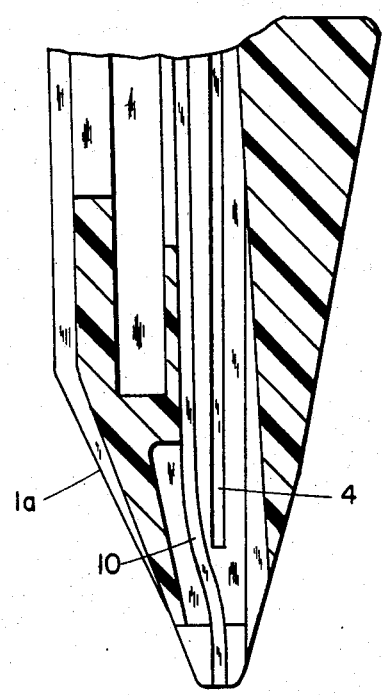
FIG. 2 is an expanded side view of the lower portion of the magazine circled in FIG. 1.
Figure 3:
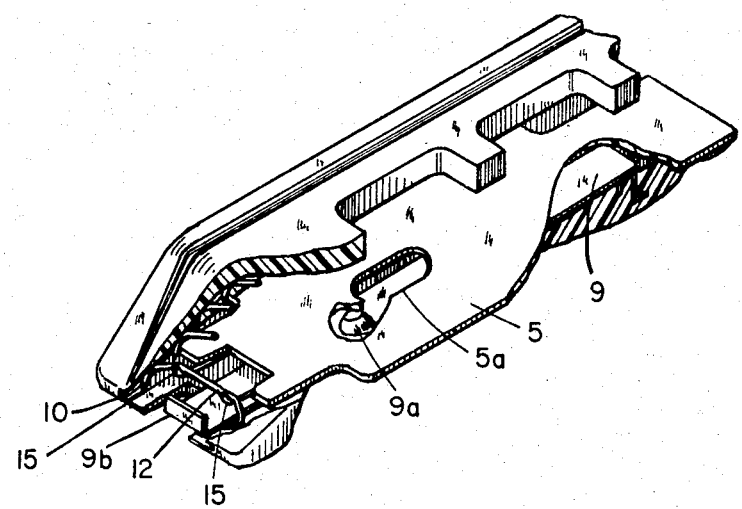
FIG. 3 is an expanded, partially cutaway and perspective view of the circled portion shown in FIG. 1, and showing the improvements in an initial position.

Referring to FIG. 1, trigger 2 is fully extended from handle 1. In FIGS. 1 and 3 (FIG. 3 is an expanded, partially cutaway and perspective view of the circled portion shown in FIG. 1), the instrument is in its rest or static condition. In FIGS. 1 and 2, the loading of the staples 12 into the staple track 10 is by feeding one staple behind the other in a point to crown configuration.

Referring again to FIG. 1, the orientation of the magazine 1a (and therefore the anvil shelf 9b in the magazine) to the handle 1 and/or the trigger 2 is not critical to the practice of this invention. That is, the orientation can be essentially perpendicular, (as shown in FIG. 1), parallel or oblique. Also, the orientation of the anvil shelf 9b to the handle 1 and/or the trigger 2 can be variable, e.g. by pivotally attaching the magazine 1a to the handle 1 and/or trigger 2.

The proximal ends of the anvil surface 9c and the hold back spring 15a can be separately or jointly imbedded in the magazine 1a by techniques known in the prior art, e.g. by molding one or more grooves in the magazine 1a.

Referring to FIG. 3, forming blade 5 is at its fully retracted position. With the forming blade 5 in this position, raised cam 9a on anvil surface 9 is out of the hole 5a of forming blade 5. The anvil surface 9b is out of alignment with staple 12 and forming blade 5. It is to be understood that the terms "cam" and "boss", as used to describe element 9a, are synonymous. It is further to be understood that the terms "hole" and "opening", as used to describe element 5a, are synonymous.

Referring further to FIG. 3, hold back spring 15 is in its undeflected position. There are two structurally and functionally identical elements 15 shown in FIG. 3 for the hold back spring. However, the elements 15 can be made as one piece. Also, the hold back spring can be made as one structural element. Therefore, the two elements 15 are jointly described as a hold back spring. The first staple 12 in the column of staples rests on hold back spring 15.

Until the forming blade 5 moves the first staple 12, the hold back spring 15 remains in its undeflected position and holds the column of staples in the track 10. In this position the hold back spring 15 offsets a negatory spring force on the column of staples. This negatory spring force is a permanent bias to the column of staples.

The use of a negatory spring as a bias for a plurality of staples is known in the prior art, e.g. as disclosed in U.S. Pat. No. 4,406,392, FIG. 8 element 7 and FIG. 9. The use of a sinusoidal advancing spring for a column of staples is also known from the prior art, e.g. as disclosed in U.S. Pat. No. 4,043,504, FIG. 4 element 41. These patents are incorporated herein by reference.

Referring to FIG. 1, the forming blade 5 can be retracted by a flange 5b on the proximal end of the forming blade. The flange fits into a groove 2d in the trigger. The motion of the forming blade 5 is thus directly dependent on the motion of the trigger 2.

Figure 4:
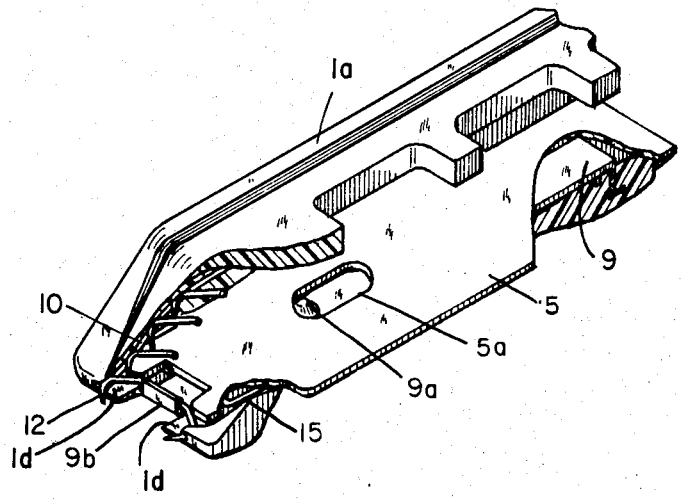
FIGS. 4 to 6 are expanded, partially cutaway and perspective views showing the improvements in an advanced, more advanced and completed advanced position, respectively.

In FIGS. 1, 2 and 4, as trigger 2 is compressed into handle 1, the forming blade 5 is caused to advance in track 4 (shown in FIG. 2) until the leading edge contacts the top of the first staple 12 in the track 10. With advance of the forming blade 5, the anvil surface cam 9a falls into hole 5a in the forming blade. This causes the anvil surface 9 to relax from its flexed position. This relaxation brings the anvil forming shelf 9b into alignment with the staple 12 in the staple track 10 and with the forming blade 5 in the forming track 4.

Preferably, the cam 9a falls into hole 5a before or as the distal portion of forming blade 5 contacts the first staple 12. This functional relationship is preferred because it allows for the anvil shelf 9b to be in alignment with the forming blade 5 and with the first staple 12 before the first staple is stripped off the hold back spring 15. That is, the anvil shelf 9b is in position to receive the first staple 12 before the first staple is stripped off the hold back spring 15.

The position of the anvil surface 9 and shelf 9b is dependent on the position of the cam 9a to the opening 5a. That is, the linear motion of the forming blade 5 causes the opening 5a to act on the cam 9a. This action simultaneously causes arcuate motion of the anvil surface 9 and the shelf 9b.

After the cam 9a moves into the opening 5a, the structural relationship between the forming blade 5 and the anvil shelf 9b is fixed, and they are in substantial alignment in the plane of the forming blade's linear motion.

Referring generally to FIGS. 1 and 4 to 7, the improved stapler can have a means to control the movement of the trigger 2 into the handle 1. An example of a control means is disclosed in U.S. application Ser. No. 321,038 filed Nov. 13, 1981 now U.S. Pat. No. 4,458,835. These references are incorporated by reference. In these references and as shown in FIG. 1 in this application, a trigger ratchet pawl 2c indirectly contacts at least one cam 1b in handle 1. This pushes the ratchet pawl 2c into a ratchet 1c. With the pawl 2c held against the ratchet 1c, trigger 2 is held in its position even though the trigger squeezing force is released.

Further, arm 2a supporting pawl 2c can be movably attached to trigger 2, e.g. as shown in FIG. 1 pivot 2b.

Alternatively, arm 2a can be permanently attached to trigger 2 as shown in the prior art references. Finally, as shown in FIG. 1 in this application, the scalloping on the contacting edges of the handle 1 and trigger 2 is optional. It is to be understood that these contacting edges can be of any geometrical configuration, i.e. straight or contoured, which will allow the trigger 2 to be compressible into the handle 1.

Figure 5:
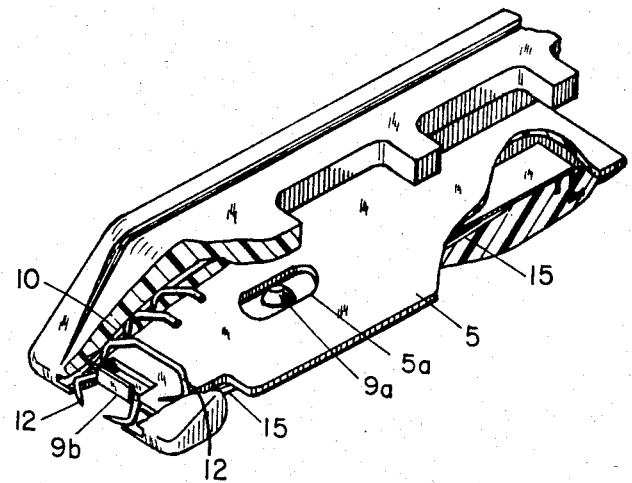

Referring to FIGS. 4 and 5, further compressing of the trigger 2 into the handle 1 causes the forming blade 5 to further advance. In FIG. 4, the staple deflects hold back spring 15, allowing escapement of the first staple 12 from the column of staples. The hold back spring 15 is held in its deflected position by being in contact with a surface of the forming blade 5. In FIG. 5, forming blade 5 carries staple 12 on track 10 forward until it is positioned against the anvil shelf 9b. The trigger pawl 2c, as shown in FIG. 1 and as disclosed in the above prior art references, is engaged by a ratchet 1c during the motion shown in FIG. 4.

Referring specifically to FIG. 4, the staple track 10 continues to hold the legs of the first staple 12 even though the points of the staple protrude from the tip of the magazine 1a. In the preferred embodiment, staple track 10 sequentially carries the first staple 12 from the column of staples to the anvil shelf 9b. However, another embodiment can be that the first staple 12 in the column of staples enters forming track 4 (shown in FIG. 2) and is then carried on track 4 to the anvil shelf 9b.

The width of the anvil shelf 9b is equal to or greater than the cross-sectional width of the staple 12. In many embodiments, because the column of staples will be circular in cross-section, the width of the staple will be equal to its diameter. If the anvil shelf width is equal to the width of the first staple, the travel of the anvil shelf 9b from the stripping surface 1d (on the magazine 1a) to a position substantially in alignment with the first staple 12 and the forming blade 5 is essentially equal to the width of the anvil shelf 9b. If the anvil shelf width is greater than the width of the staple, the travel of the anvil shelf 9b is essentially equal to or less than the width of the anvil shelf.

As shown in FIG. 5, a surface of the forming blade 5 retains the column of staples 12 in the staple track 10. In summary, and as also shown in FIGS. 2, 4 and 6, one side of the forming blade 5 holds the column of staples 12, and the other side of the forming blade holds spring 15 from moving, after the forming blade 5 is advanced past the hold back spring 15.

Figure 6:
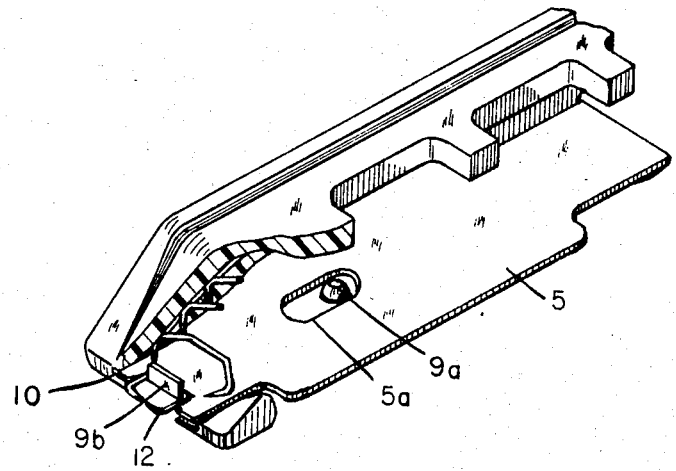

In FIGS. 1 and 6, the trigger 2 is squeezed into handle 1 to the end of its stroke. This causes the forming blade 5 to fully advance, which bends the first staple 12, around anvil shelf 9b until it is fully formed. The forming of a staple around an anvil flange is well known in the prior art, e.g. as disclosed in U.S. Pat. No. 4,014,492 issued Mar. 29, 1977, which is incorporated herein by reference.

Anvil shelf 9b remains in alignment with the forming blade 5. The two legs of the formed staple perpendicular to the crown are backed by a staple stripping area 1b (more fully shown in FIG. 4) at the distal end of magazine 1a.

The trigger ratchet pawl 2c becomes inactive as or after the forming blade 5 is fully advanced. This is because the ratchet pawl indirectly falls off the cam 1b, allowing the trigger 2 to return to its initial rest position.

In FIG. 6, hold back spring 15 and the column of staples 12 continue to be held by the forming blade 5.

Figure 7:
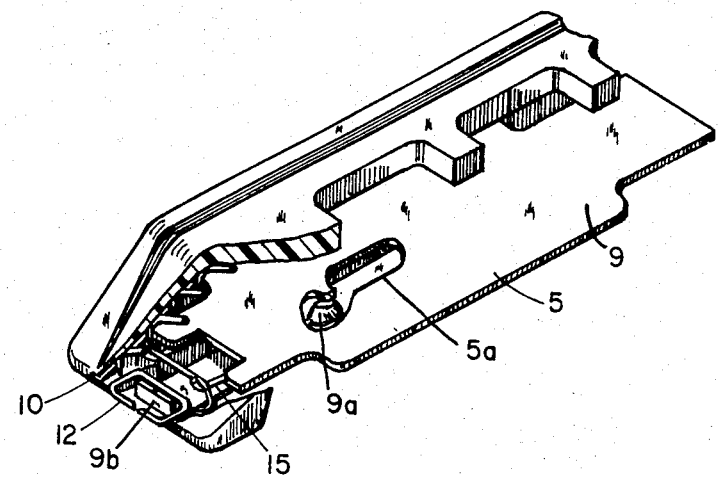
FIG. 7 is an expanded, partially cutaway and perspective view showing the relationship of the improvements in position retracted from FIG. 6.

In FIGS. 1 and 7, the trigger 2 is released. This allows the trigger 2 to return to its initial (fully opened) position. As stated above in describing FIG. 6, this is because the trigger pawl 2c is functionally inoperative after the pawl rides over the cam 1b.

Referring specifically to FIG. 7, the forming blade 5 retracts. This allows the hold back spring 15 to relax and move into its initial rest position. In this position and after the forming blade 5 retracts a sufficient distance, the second staple in the column of staples moves down the staple track 10 until it is arrested by the hold back spring 15. It is to be understood that the remaining staples in the column of staples simultaneously move down the track with the second staple.

At approximately the end of the forming blade stroke, the anvil cam 9a is forced to ride out of the hole 5a. This causes the anvil surface 9 and the shelf 9b to flex toward the position shown in FIG. 3. As the anvil shelf 9b flexes, the formed staple 12 is separated from the anvil shelf 9b by the stripping surface 1d (more fully shown in FIG. 4) on the magazine 1a.

Referring to FIGS. 6 and 7, the bottom of the stripping surface 1d is in a plane equal to or below one-half of the cross-sectional height of the staple crown 12 (on the anvil shelf 9b). For a staple having a circular cross-section, one-half the height is equal to the radius.

What is claimed is:

1. A surgical stapler comprising a housing, means for forming a staple, said forming means having an anvil surface terminating in a movable flange and a staple forming track movable containing a forming blade, said anvil surface having a boss and said forming blade having an opening, said anvil surface boss having an arcuate motion dependent on the linear motion of said forming blade opening such that said boss moves into said opening as said forming blade approaches said flange, and said boss moves out of said opening as said forming blade retracts from said flange, a staple feed track movably containing a plurality of staples in a point-to-crown configuration, the holding portion of said feed track being substantially parallel to said forming track and the distal, escaping, portion of said feed track being in substantial alignment with the distal portion of said forming track, and means for activating said forming means said activating means being cooperatively attached to said forming means.

2. A surgical stapler as in claim 1 further comprising a formed staple stripping surface adjacent at least two opposing sides of said anvil flange and wherein said stationary stripping surface is contained on said housing.

3. A surgical stapler as in claim 1 wherein said housing has a handle.

4. A surgical stapler as in claim 3 wherein said anvil surface and flange is biased relative to said forming blade.

5. A surgical stapler as in claim 4 wherein said anvil surface and flange is cantilevered.

6. A surgical stapler as in claim 5 wherein said boss moves into said opening essentially after zero travel of said forming blade toward said anvil flange such that said anvil flange is in substantial alignment with said forming blade before or as the distal portion of said forming blade contacts the proximal staple from said plurality of staples.

7. A surgical stapler as in claim 3 wherein said boss moves into said opening essentially after zero travel of said forming blade toward said anvil flange such that said anvil flange is in substantial alignment with said forming blade before or as the distal portion of said forming blade contacts the proximal staple from said plurality of staples.

8. A surgical stapler comprising means for forming a staple, said forming means having an anvil surface terminating in a movable flange and a staple forming track movably containing a forming blade, said anvil surface having a boss and said forming blade having an opening, said anvil surface boss having an arcuate motion dependent upon the linear motion of said forming blade opening such that said boss moves into said opening as said forming blade approaches said flange, and said boss moves out of said opening as said forming blade retracts from said flange so that said anvil flange is in substantial alignment with said forming blade when said boss is in said opening so that a staple can be formed on said anvil flange by said forming blade, a staple feed track movably containing a plurality of staples in a point-to-crown configuration, the holding portion of said feed track being in substantial alignment with the distal portion of said forming track, and means for activating said forming means, said activating means being cooperatively attached to said forming means.

9. A surgical stapler as in claim 8 wherein said boss moves into said opening essentially after zero travel of said forming blade toward said anvil flange such that said anvil flange is in substantial alignment with said forming blade before or as the distal portion of said forming blade contacts the proximal staple from said plurality of staples.

10. A surgical stapler as in claim 8 wherein said anvil surface and flange are biased relative to said forming blade.

11. A surgical stapler as in claim 10 wherein said anvil surface and flange are cantilevered.

12. A surgical stapler as in claim 11 wherein said boss moves into said opening essentially after zero travel of said forming blade toward said anvil flange such that said anvil flange is in substantial alignment with said forming blade before or as the distal portion of said forming blade contacts the proximal staple from said plurality of staples.

* * * * *